United States Patent [19]

Uchiyama et al.

[11] Patent Number: 5,057,418
[45] Date of Patent: Oct. 15, 1991

[54] PROCESS FOR THE PREPARATION OF DIFRUCTOSE DIANHYDRIDE III

[75] Inventors: Takao Uchiyama, Minoo; Kuniji Tanaka, Nishinomiya; Mishio Kawamura, Toyonaka, all of Japan

[73] Assignee: Mitsubishi Kasei Corporation, Tokyo, Japan

[21] Appl. No.: 318,255

[22] Filed: Mar. 3, 1989

[30] Foreign Application Priority Data

Mar. 7, 1988 [JP] Japan .................................. 63-53164

[51] Int. Cl.$^5$ ........................ C12P 19/14; C12P 19/12; C12R 1/06
[52] U.S. Cl. ........................................ 435/99; 435/74; 435/97; 435/100; 435/101; 435/105; 435/193; 435/830
[58] Field of Search ................... 435/97, 89, 100, 101, 435/105, 74, 193, 830

[56] References Cited

FOREIGN PATENT DOCUMENTS 56-26400   6/1981  Japan .
63-275694 11/1987  Japan .
62-275694 11/1987  Japan .
63-219372  9/1988  Japan .
63-219389  9/1988  Japan .

OTHER PUBLICATIONS

Biotech Derwent Abstract 89-03534, Kawamura et al., A BCHA6 Agric. Biol. Chem. (1985), 52, 12, 3209-3210.
J. Biochem., vol. 78, No. 6, 1975; "Enzymic Hydrolysis of Di-D-Fructofuranose 1, 2'; 2, 3' Dianhydride with *Arthrobacter Ureafaciens*", T. Tanaka, et al., pp. 1201-1206.
Carbohydrate Research, vol. 101, 1982; "Anomeric Configurations of Di-D-Fructose Anhydride III, Produced by Inulin D-Fructotransferase", T. Uchiyama et al., pp. 138-140.
Carbohydrate Research, vol. 107, 1982; "The Crystal Structure of Di-D-Fructose Anydride III, Produced by Inulin D-Fructotransferase", T. Taniguchi et al., pp. 255-262.
Agric. Biol. Chem., vol. 47, No. 2, 1983; "Formation of Di-D-Fructose Anhydrade III from Inulin by the Root of *Lycoris Radiata* Herbert", T. Uchiyama et al., pp. 437-439.
Agric. Biol. Chem., vol. 47, No. 12, 1983; "Effects of Some Substances on the Formation of Inulin Fructotransferase in *Arthrobacter Ureafaciens*", M. Nakayama, pp. 2761-2766.
Patent Abstracts of Japan, vol. 12, No. 165 (C-496), [3012], 18th May, 1988, p. 89, JP-A-62 275 694 (Natl. Food Res. Inst. (30-11-1987).
Agricultural and Biological Chemistry vol. 52, No. 12, Dec. 1988, pp. 3209-3210, The Agricultural Chemical Society of Japan; M. Kawamura et al., "Purification and Some Properties of Inulin Fructotransferase (Depolymerizing) from Arthobacter Ilicis".
Zentralblatt Bakteriol. Mikrobiol. Hyg. I. Abt. Orig., C2, 1981, pp. 318-323; M. D. Collins et al.: "Reclassification of *Corynebacterium Ilicis* (Mandel, Guba and Litsky) in the Genus Arthrobacter, as Arthrobactor Ilicis Comb. Nov.", p. 321, line 31, p. 322, line 17.

*Primary Examiner*—Herbert J. Lilling
*Attorney, Agent, or Firm*—Oblon, Spivak, McClelland, Maier & Neustadt

[57] ABSTRACT

Disclosed herein is a process for preparing difructose dianhydride III (DFA III) comprising reacting inulin with an inulin lytic enzyme derived from a microorganism belonging to *Arthrobacter ilicis*. The enzyme employed herein efficiently produces DFA III from inulin and is more stable against heat than conventional enzymes. The present process enables industrial continuous production of DFA III. The preferred strain used herein is *Arthrobacter ilicis* MCI 2297 (FERM P-9893).

1 Claim, No Drawings

PROCESS FOR THE PREPARATION OF DIFRUCTOSE DIANHYDRIDE III

BACKGROUND OF THE INVENTION

1. Field of the Invention

The present invention relates to a process for preparing difructose dianhydride III, hereinafter referred to as "DFA III".

2. Description of the Prior Art

DFA III is a disaccharide having the structure in which two molecules of fructose are condensed with dehydration via 1-2' and 2-3' linkages, and has been isolated and identified in 1931 by Jackson et al.: *Bur. stand. J. Res.*, 6, 709 (1931).

DFA III may notably be regarded as a low-calorie sweetener since it is not metabolized nor fermented in animal bodies and is expected to be utilized in various applications, including use for a diet food, in the future.

Jackson et al. (supra) prepared DFA III by acid hydrolysis from inulin, which is a polysaccharide mainly composed of fructose. However, the yield was merely no more than about 2%. Thus, the process employed by them is not efficient.

In 1972, Tanaka et al. prepared DFA III from inulin by means of an inulin lytic enzyme produced by *Arthrobacter ureafaciens*: *Biochim. Biophys. Acta*, 284, 248 (1972). However, this enzyme is highly sensitive to temperature; it will be rapidly inactivated above 60° C. Thus, this enzyme cannot be suitable for industrial production of DFA III.

SUMMARY OF THE INVENTION

The present inventors have made great efforts to solve these problems in the prior art and found that an inulin lytic enzyme derived from a microorganism belonging to *Arthrobacter ilicis* can be used to efficiently produce DFA III and that this enzyme has higher stability against heat as compared with conventional ones enabling industrially efficient continuous production of DFA III. Thus, the present invention has been attained.

Accordingly, it is a primary object of the present invention to provide an efficient process for preparing DFA III.

Another object of the invention is to provide a novel process which permits industrial continuous production of DFA III.

A further object is to provide an inulin lytic enzyme which can be effectively used in the present process for the production of DFA III.

A still another object of the invention is to provide a microorganism strain capable of producing said inulin lytic enzyme.

Other objects and advantages of the present invention will be apparent from the detailed description thereof as set forth hereinbelow.

According to the present invention, there is provided a process for preparing difructose dianhydride III (DFA III) comprising reacting inulin with an inulin lytic enzyme derived from a microorganism belonging to *Arthrobacter ilicis*, in a solution containing inulin.

DESCRIPTION OF THE INVENTION

The present invention will hereinafter be described in detail.

Inulin lytic enzymes which can be used in the present invention are derived from microorganisms which belong to *Arthrobacter ilicis*.

Such microorganisms belonging to *Arthrobacter ilicis* may include, for example, *Arthrobacter ilicis* MCI 2297 deposited on Feb. 25, 1988 with the Germentation Research Institute, Agency of Industrial Science and Technology, Ministry of International Trade and Industry, Japan under Accession No. FERM P-9893, which was converted to the deposition according to Budapest Treaty on Feb. 9, 1989 under No. FERM BP-2279.

The *Arthrobacter Ilicis* MCI 2297, hereinafter abbreviated as "MCI 2297", was isolated from natural soil by the present inventors. The microbial properties of the strain are summarized as follows:

1. Microscopic Characteristics:

Characteristics of Colonies Cultured for One Week in Heart Infusion Agar Medium at 30° C.

| | |
|---|---|
| (1) Shape of colony: | Circular shape |
| (2) Size: | 2 to 3 mm in diameter |
| (3) Upheaval of the surface: | Convex enation in the surface |
| (4) Appearance of the surface: | Smooth surface |
| (5) Gloss: | Dull |
| (6) Color: | Yellowish grey |
| (7) Transparency: | Translucent |
| (8) Periphery: | Entire |

Morphological Properties of Cells Cultured for 3 to 24 Hours in Heart Infusion Agar Medium at 30° C.

(1) Cell Morphology: Cells unevenly grow to form elongated rods during an initial culture period of up to about 6 to 8 hours. A septum is then formed at the central portion in the cell. The cells curve and cell division is gradually repeated. After 12 hours are passed, most cells are changed into uniform short rod-like.
(2) Type of Cell Division: Bending type.
(3) Motility: Yes
(4) Spore Formation: No
(5) Gram Staining: Cells show strong gram positivity early in the culture; as the time is passed, the cells gradually become gram-negative (i.e., gram-variable).
(6) Acid-fastness: Negative.

2. Physiological Properties

| | | Strain MCI 2297 | *Arthrobacter ilicis* DSM 20138 |
|---|---|---|---|
| (1) | Growth in Anaerobic Conditions | − | − |
| (2) | Growth in Air | + | + |
| (3) | Catalase Activity | + | + |
| (4) | Oxidase Activity | − | − |
| (5) | O-F Test | F | O |
| (6) | Reduction of Nitrate Salts | − | − |
| (7) | Hydrolysis of Gelatin | + | + |
| (8) | Hydrolysis of Casein | + | + |
| (9) | Hydrolysis of Starch | + | − |
| (10) | Utilization of Chitin | + | + |
| (11) | Utilization of Cellulose | + | + |
| (12) | Utilization of Tween 20 | + | − |
| (13) | Utilization of Tween 60 | + | − |
| (14) | Utilization of Tween 80 | − | − |
| (15) | Utilization of Xanthine | + | + |
| (16) | Utilization of Tyrosine | + | + |
| (17) | Production of Indole | − | − |
| (18) | Methyl Red Reaction | − | − |
| (19) | Urease Activity | − | − |
| (20) | Phosphatase Activity | + | + |
| (21) | DNase | + | + |
| (22) | V.P Test | − | − |
| (23) | Growth in 5% Saline | + | + |
| (24) | Growth in 10% Saline | − | − |

-continued

2. Physiological Properties

| | | Strain MCI 2297 | Arthrobacter ilicis DSM 20138 |
|---|---|---|---|
| (25) | Growth at 4° C. | − | + |
| | 10° C. | + | + |
| | 20° C. | + | + |
| | 26° C. | + | + |
| | 30° C. | + | + |
| | 37° C. | − | − |

Utilization of Carbohydrates (Production of Acids):
Results of 14 Days Culture

| | Saccharide | | |
|---|---|---|---|
| (1) | L-arabinose | − | − |
| (2) | Xylose | − | − |
| (3) | Rhamnose | − | − |
| (4) | Glucose | − | − |
| (5) | Fructose | − | + |
| (6) | Mannose | − | − |
| (7) | Galactose | − | − |
| (8) | Sorbose | − | − |
| (9) | Sucrose | ± | − |
| (10) | Lactose | − | − |
| (11) | Maltose | − | − |
| (12) | Trehalose | − | − |
| (13) | Cellobiose | − | − |
| (14) | Raffinose | − | − |
| (15) | Dextrin | − | − |
| (16) | Starch | − | − |
| (17) | Inulin | − | − |
| (18) | Glycerol | + | ± |
| (19) | Erythritol | − | − |
| (20) | Adonitol | − | − |
| (21) | Mannitol | − | − |
| (22) | Dulcitol | − | − |
| (23) | Sorbitol | − | − |
| (24) | Inositol | − | − |
| (25) | Arbutin | ± | ± |
| (26) | Aesculin | − | − |
| (27) | Salicin | − | − |
| (28) | Alpha-methylglucoside | − | − |

Utilization of Organic Acids

| | Organic Acid | | |
|---|---|---|---|
| (1) | Acetic acid | + | + |
| (2) | Pyruvic acid | + | + |
| (3) | L-lactic acid | + | + |
| (4) | Malic acid | + | + |
| (5) | Succinic acid | + | + |
| (6) | Fumaric acid | + | + |
| (7) | Alpha-ketoglutaric acid | + | + |
| (8) | Citric acid | + | + |
| (9) | Formic acid | + | + |
| (10) | Propionic acid | + | + |
| (11) | Butyric acid | + | + |
| (12) | Oxalic acid | − | ± |
| (13) | Malonic acid | − | ± |
| (14) | Adipic acid | + | ± |
| (15) | Pimelic acid | − | ± |
| (16) | Glycolic acid | ± | ± |
| (17) | Hippuric acid | + | + |
| (18) | Uric acid | + | + |
| (19) | Glutaric acid | + | + |

3. Biochemical Properties

| Properties | Strain MCI 2297 | A. ilicis DSM 20138 |
|---|---|---|
| (1) GC content in DNA | 62.5% | 61.5% |
| (2) Major cell wall amino acid | Lysine | Lysine |
| (3) Peptidoglycan type | Lys—Ala—Thr—Ala | Lys—Ala—Thr—Ala |
| (4) Major cell wall sugars | Galactose Rhamnose Mannose | Galactose Rhamnose Mannose |
| (5) Glycolate test | Acetyl | Acetyl |
| (6) Major menaquinone | MK-9($H_2$) | MK-9($H_2$) |

4. Taxonomic Identification

1)

The present strain, MCI 2297, is an obligate aerobe showing polymorphism of rods-coccus in the cell cycle, produced no acid from carbohydrates such as glucose, and has lysine as a major amino acid in the cell wall. Thus, the strain has been found to belong to the genus Arthrobacter of irregular, nonsporing, gram positive rods as described in Bergey's Manual of Systematic Bacteriology, Vol. 2.

2) Species Level

Up to now, approximately 18 species of bacteria have been found to belong to the genus Arthrobacter. These species are distinguished from each other by their physiological and biochemical properties. In particular, the differences in the menaquinone composition and in the cross-linking peptide structure and sugar composition in their cell walls are regarded as important bases for differentiation of the species: K. H. Schleifer & O. Kandler, *Bacteriol. Rev.*, Vol. 36, 404–477 (1972); Bergey's Manual Systematic Bacteriology, Vol. 2.

The present strain MCI 2297 (a) contains MK-9($H_2$) as the major menaquinone; (b) has the cross-linking peptide structure, Lys-Ala-Thr-Ala, in the cell wall; (c) comprising galactose, rhamnose and mannose as the major sugar in the cell wall; and (d) is motile. Thus, these biochemical and morphological characteristics agree well with those of *Arthrobacter ilicis* as described in Bergey's Manual Systematic Bacteriology.

Various physiological and biochemical properties as originally described in M. D. Collins, *Zentralbl. Bakteriol. Mikrobiol. Hyg. I Abt. Orig.* C2, 318–323, (1981) for the present strain MCI 2297 were compared with those for the type strain of *Arthrobacter ilicis*, DSM 20138. The results are shown hereinbefore.

The present strain MCI 2297 and the type strain *A. ilicis* were approximately identical to each other in both the utilization patterns of saccharides and organic acids and in the biochemical properties. However, there were some differences in the utilization of Tween 20 and 60, fructose and sucrose, the hydrolysis of starch, and growth at 4° C.

These differences are assumed to be due to any difference between strains of a single species and are not considered to be inherent in and characteristic of the species. In the present invention, therefore, the above stated biochemical properties were taken as the bases for identification of the species. Thus, the present strain MCI 2297 was identified as belonging to *Arthrobacter ilicis*.

In the present invention, the strain can be easily proliferated by culturing in a medium containing nutrients utilizable by usual microorganisms. Such nutrients may include glucose, thick malt syrup, dextrin, sucrose, starch, molasses, animal and vegetable oil. Nitrogen sources such as soybean flour, wheat germ, corn steep liquor, cotton seed meal, meat extract, peptone, yeast extract, ammonium sulfate, sodium nitrate, and urea can also be used. Optionally, mineral salts capable of releasing sodium, potassium, calcium, magnesium, cobalt, chloride, phosphate, sulfate and other ions may advantageously be added.

According to the present invention, an inulin lytic enzyme derived from a bacterium belonging to the above mentioned *Arthrobacter ilicis* is contacted with a solution containing, as a single carbon source, either inulin or a liquid extract from a plant with a high inulin content, such as Jerusalem artichoke (*Helianthus tuberosus*) and burdock (*Arctium lappa*). Such a bacterium as specified above may be employed as it is or, alternatively, such an inulin lytic enzyme can be extracted from the bacteria and then used in the reaction.

When such a bacterium per se is used, the bacterium is inoculated into a culture medium containing about 1 to 10% inulin as a carbon source and subjected to shaking culture. The medium may also contain a nitrogen source such as, for example, soybean flour, wheat germ, corn steep liquor, cotton seed meal, meat extract, peptone, yeast extract, ammonium sulfate, sodium nitrate, or urea, and optionally mineral salts capable of releasing sodium, potassium, calcium, magnesium, cobalt, chloride, phosphate, sulfate and other ions. Preferably, the temperature is in the range of 20 to 37° C. and the time period is in the range of 12 to 40 hours in the shaking culture. The resultant culture is centrifuged to remove bacteria and the supernatant is heat treated to inactivate the enzyme. After concentration, the material is chromatographed, for example, on an active carbon column. After elution of fructose by distilled water, elution is effected by 5% aqueous ethanolic solution. DFA III produced during this fractionation is then concentrated to dryness.

When such an inulin lytic enzyme as described above is employed in the reaction, the culture obtained by the above described procedures is first centrifuged to remove bacteria. To the filtrate, 65% saturated ammonium sulfate solution is added to salt out, and the resulting precipitate is collected by centrifugation, suspended into a small amount of water and dialyzed to produce a crude enzyme preparation. This crude enzyme preparation may also be contacted with inulin in, for example, 0.01–0.1 M phosphate buffer at pH 7.0.

The crude enzyme preparation may be purified by ion-exchange chromatography on DEAE-Toyopearl 650M or SP-Toyopearl 650M column to yield an enzyme preparation showing a single electrophoretic band. This purified enzyme preparation had an optimum pH of 5.5 and showed a maximal activity at 60° C. However, it could be stable in a wide pH range of 4.0 to 11.0 and at a temperature up to 70° C. for 30 minutes heat treatment. Thus, this enzyme preparation showed a high temperature stability.

The inulin lytic enzyme derived from a bacterium belonging to *Arthrobacter ilicis* according to the present invention produces DFA III in a good yield and is much more stable to heat as compared with conventional enzymes. Thus, the enzyme of the present invention may be effective for the continuous production of DFA III.

EXAMPLES

The following examples will be given by way of illustration of the present invention but not by way of limitation. It will be understood by those skilled in the art that many variations and modifications may be made in the preferred embodiments of the present invention without departing from the spirit and scope of the present invention as defined in the attached claims.

EXAMPLE 1

A culture medium (150 ml) containing 5% commercially available inulin, 0.02% yeast extract, 0.2% sodium nitrate, 0.05% magnesium sulfate, 0.05% potassium chloride, 0.05% potassium dihydrogenphosphate and 0.001% ferric chloride, adjusted to pH 7.0, was sterilized with steam at 120° C. for 20 minutes. The sterilized solution in flask was inoculated with one platinum loopful of MCI 2297 strain. The inoculated solution was incubated at 30° C. for 30 hours on a rotary shaker at 160 r.p.m.

After culture, the cells were removed by centrifugation. The resulting filtrate was heat treated for 10 minutes to inactivate enzymes and then concentrated under reduced pressure to approximately 10 ml. This concentrate was adsorbed onto a column to which 30 g active carbon and 60 g Celite No. 535 had been filled by distilled water, washed with one liter distilled water, and eluted with 5% aqueous ethanol.

The eluted peaks were collected and concentrated under reduced pressure to dryness to yield DFA III. The yield of DFA III was 10% based on the starting inulin. Thin layer chromatography on silica gel plate, Merck, with n-butanol/ethanol/water 2/1/1 (v/v/v) as developing solution showed the same Rf value, 0.67, as that of standard DFA III obtained by acid decomposition of inulin.

EXAMPLE 2

The filtrate (1 ml) obtained in Example 1 was added to 0.05 M phosphate buffer (4 ml) containing 10% inulin and reacted overnight at 30° C.

The reaction mixture was heated to inactivate the enzyme, chromatographed on an active carbon column, and eluted with 5% ethanol. The eluate was concentrated under reduced pressure to dryness to yield DFA III with a yield of 30% based on the starting inulin.

What is claimed is:

1. A process for preparing difructose dianhydride III (DFA III) comprising reacting inulin with an inulin lytic enzyme derived from *Arthrobacter ilicis* strain MCI 2297 (FERM BP-2279), in a solution containing inulin.

* * * * *